United States Patent [19]
Linden et al.

[11] Patent Number: 5,644,922
[45] Date of Patent: Jul. 8, 1997

[54] CYLINDRICAL CHAMBER FOR THE RAPID COOLING AND WARMING OF SAMPLES BETWEEN ROOM AND CRYOGENIC TEMPERATURES IN A DRY GAS ATMOSPHERE

[75] Inventors: Derek S. Linden, Hanscom AFB; Daniel E. Godin, Saugus, both of Mass.

[73] Assignee: The United States of America as represented by the Secretary of the Air Force, Washington, D.C.

[21] Appl. No.: 521,206

[22] Filed: Aug. 30, 1995

[51] Int. Cl.⁶ .................................................. F25B 19/00
[52] U.S. Cl. .................................................. 62/51.1; 62/78
[58] Field of Search .................................. 62/45.1, 51.1, 62/78

[56] References Cited

U.S. PATENT DOCUMENTS

| | | | |
|---|---|---|---|
| 3,195,620 | 7/1965 | Steinhardt, Jr. | 62/51.1 |
| 4,232,453 | 11/1980 | Edelmann | 62/51.1 |
| 4,459,823 | 7/1984 | Josephs et al. | 62/51.1 |
| 4,480,682 | 11/1984 | Kaneta et al. | 62/51.1 |
| 4,485,641 | 12/1984 | Angelier et al. | 62/51.1 |
| 4,566,283 | 1/1986 | Boese | 62/51.1 |
| 4,606,195 | 8/1986 | Winkler | 62/45.1 |
| 4,757,692 | 7/1988 | McDonald | 62/51.1 |
| 5,052,183 | 10/1991 | Koscica et al. | 62/51.1 |
| 5,166,776 | 11/1992 | Dederer et al. | 62/51.1 |
| 5,241,828 | 9/1993 | Kapitulnik | 63/3.2 |
| 5,275,016 | 1/1994 | Chatlerjee et al. | 62/381 |
| 5,346,570 | 9/1994 | Warden et al. | 156/191 |
| 5,355,456 | 10/1994 | Osofsky | 392/342 |
| 5,357,758 | 10/1994 | Andonian | 62/45.1 |
| 5,361,588 | 11/1994 | Asami et al. | 62/6 |
| 5,373,701 | 12/1994 | Siefering et al. | 62/48.1 |
| 5,385,010 | 1/1995 | Horn | 62/6 |
| 5,417,072 | 5/1995 | Silver et al. | 62/51.1 |

*Primary Examiner*—Ronald C. Capossela
*Attorney, Agent, or Firm*—William G. Auton

[57] ABSTRACT

The cylindrical chamber allows one to quickly package a test fixture with attached sample, cool it to liquid-nitrogen temperature in a few minutes, and warm it back up to room temperature in a few minutes in a dry, helium or nitrogen atmosphere, which prevents water or ice from condensing on the test fixture and sample.

7 Claims, 2 Drawing Sheets

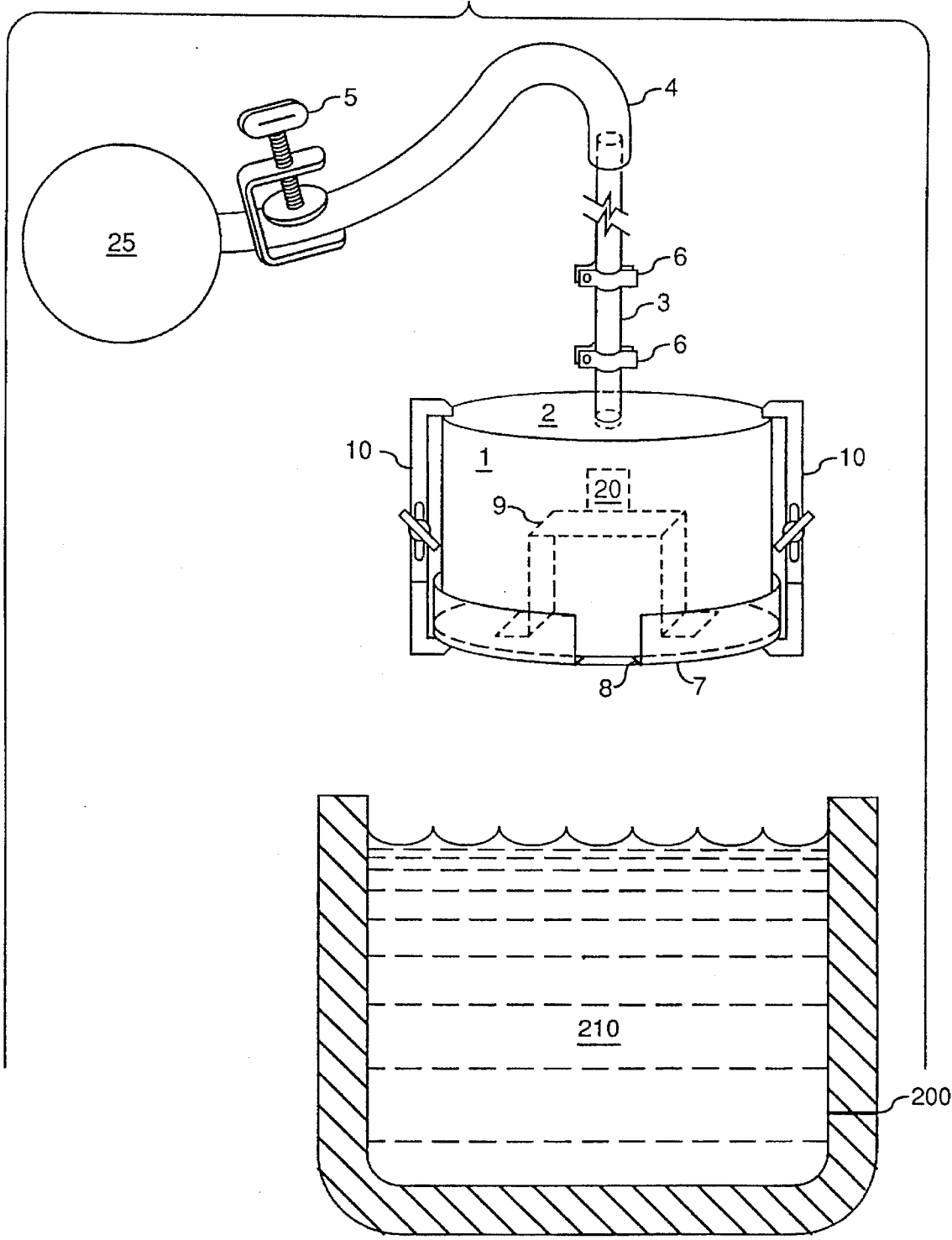

CYLINDRICAL CHAMBER FOR THE RAPID COOLING AND WARMING OF SAMPLES BETWEEN ROOM AND CRYOGENIC TEMPERATURES IN A DRY GAS ATMOSPHERE

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to cryogenic cooling systems and more specifically the invention pertains to a system for the rapid temperature adjustment of samples between cryogenic temperatures and room temperatures.

The simplest way to cool something to liquid nitrogen temperature is to immerse it in liquid nitrogen. However, doing so usually allows impurities to cling to the object immersed, since liquid nitrogen generally is not completely pure. In addition, warming the sample from liquid nitrogen to room temperature in room air allows water to condense and/or freeze on the surface of the sample. For samples sensitive to water damage, such as high-temperature superconductors, this option is unattractive. In addition, simply encasing the object in some kind of rubber or latex sheath provides a non-durable, difficult to implement, and unreliable solution.

The task of adjusting the temperatures of samples between cryogenic and room temperatures is alleviated, to some extent, by the systems disclosed in the following U.S. patents, the disclosures of which are incorporated herein by reference:

U.S. Pat. No. 5,385,010 issued to Horn;
U.S. Pat. No. 5,373,701 issued to Siefering;
U.S. Pat. No. 5,361,588 issued to Asami;
U.S. Pat. No. 5,357,758 issued to Andonian;
U.S. Pat. No. 5,355,456 issued to Osofsky;
U.S. Pat. No. 5,346,570 issued to Warden;
U.S. Pat. No. 5,275,016 issued to Chatlerjee; and
U.S. Pat. No. 5,241,828 issued to Kapitulnik.

There are many different types of dewars for cooling samples to liquid nitrogen temperatures that keep the sample dry. However, they can take hours to cool down, and cost thousands of dollars to purchase. Also, they can require large amounts of liquid nitrogen to operate compared with the invention described here. They usually use one of two methods for keeping the sample clear of liquid coolant and water: vapor flow, and vacuum chamber. A vapor flow system allows the coolant (liquid nitrogen or helium) to evaporate and blows vapor across the sample. This increases the time required to cool down the sample and the complexity of the mechanism. The other method is placing the sample in a vacuum chamber, in contact with a piece of metal or other conductor of heat which is in turn in contact with the coolant. This method keeps all contaminating substances (like moisture-laden air and the liquid coolant) away from the sample, but also increases the time to cool the sample and the complexity of the device. Vacuums are difficult to obtain and maintain in a cryogenic environment if the seals are placed at cryogenic temperatures. Therefore, sample chambers often have to have the vacuum seal placed above the coolant level, which increases the size of the sample chamber and the difficulty of changing the sample. If the vacuum seal is placed below the coolant level, it requires a seal made of indium, which maintains its integrity at cryogenic temperatures, but is difficult to open and close.

SUMMARY OF THE INVENTION

The present invention is a cryogenic temperature adjustment system for cooling a test sample to near cryogenic temperatures in a moisture-free environment. The term "cryogenic temperature" means a temperature near the boiling points of liquid nitrogen or liquid helium. The preferred embodiment of the invention includes: a chamber which holds the test sample in an enclosed internal atmosphere of a moisture-free gas (or a "dry gas" such as helium or dry nitrogen); a controllable supply of the moisture-free gas; and a container of a cryogenic liquid (such as liquid nitrogen or liquid helium) into which the chamber is placed. The above cited patents describe elements of dewar chamber systems that are useable in the present invention.

An internal heating unit can be used to warm the chamber and test sample back to room temperatures when required. Suitable heaters can include: an electrical space heating unit (which blows a warm stream of air upon the chamber when the chamber is removed from the container) or electrical heating circuits of nichrome wire which has an electrical impedance that causes the wire to heat up when conducting an electrical current.

It is an object of the present invention to provide a cryogenic temperature adjustment system which allows an object of interest to be cooled to cryogenic temperatures without external water or ice condensing on the object of interest.

It is another object of the present invention to provide a cryogenic temperature adjustment system which enables a cooled object of interest to be heated quickly back to room temperatures.

These objects together with other objects, features and advantages of the invention will become more readily apparent from the following detailed description when taken in conjunction with the accompanying drawings wherein like elements are given like reference numerals throughout.

DESCRIPTION OF THE DRAWINGS

The invention will become more apparent from the following detailed specification and drawings in which;

FIG. 2 is a view of the cooling chamber system of the present invention when assembled.

DETAILED DESCRIPTION OF THE PREFERRED EMBODIMENT

Figure 1:
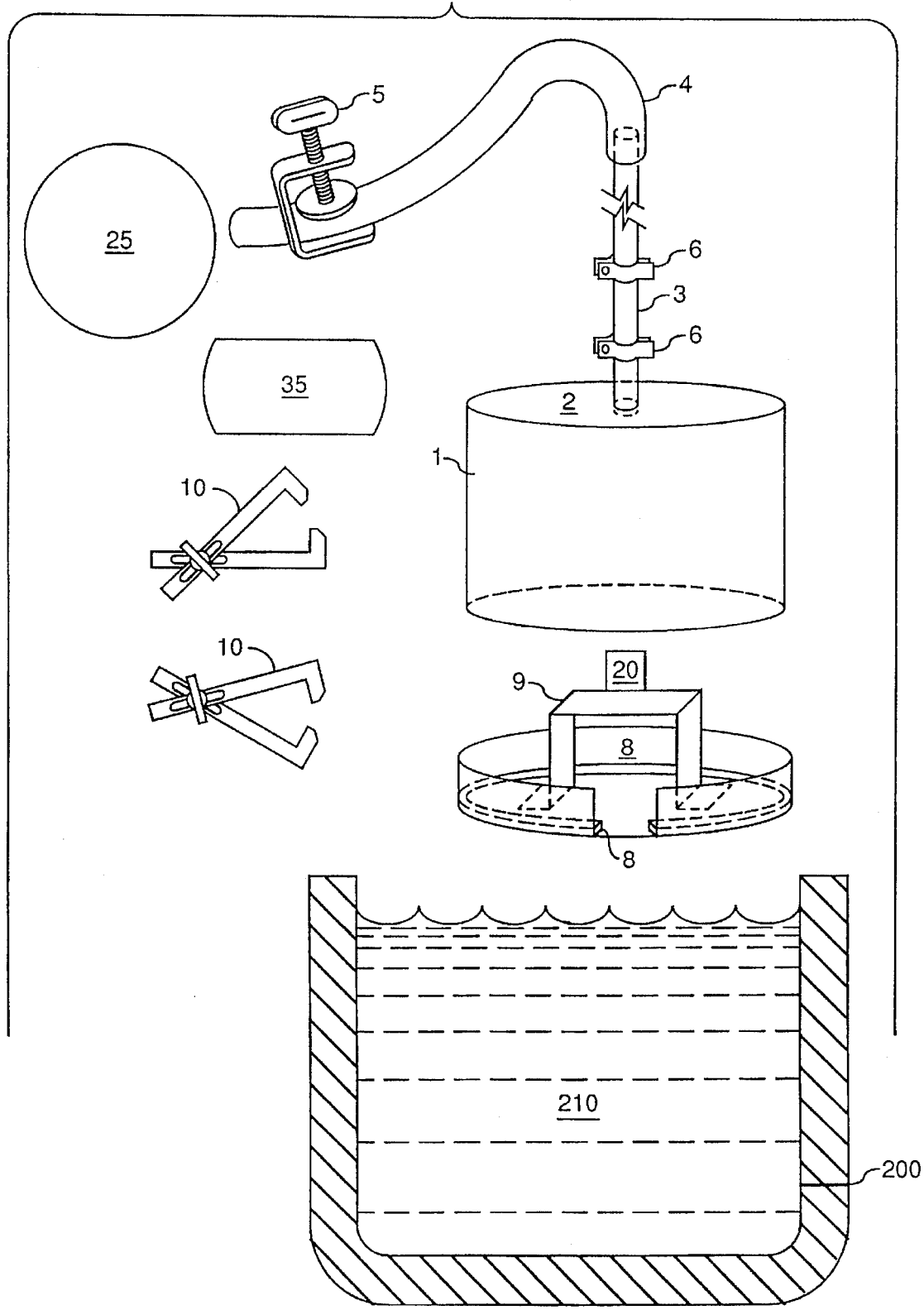
FIG. 1 is an exploded view of the present invention.

The present invention is a cryogenic chamber system that accelerates the rate of cooling and the rate of warming of samples between cryogenic temperatures and room temperatures.

FIG. 1 is an exploded view of the present invention; and

FIG. 2 is a view of the cooling chamber system of the present invention when assembled. As mentioned earlier, the above-cited patents have conventional elements of dewar systems that are usable in the present invention, and it is not necessary to describe these elements in detail. The preferred embodiment of the invention includes: a chamber composed of two sections 1 and 8 form a shell which holds a test sample 20 in an enclosed internal atmosphere of a moisture-free gas (such as helium or dry nitrogen); a controllable supply 25 of the moisture-free gas; and a container 200 of a cryogenic liquid 210 (such as liquid nitrogen or liquid helium) into which the chamber is placed. A heating unit 35 can be used to warm the chamber and test sample back to room temperatures when required, or be used to set the test sample temperature at a value between room temperature and the coolant temperature.

A controlled decrease in temperature is possible if the chamber is not totally immersed in liquid nitrogen. If the chamber is held above the liquid nitrogen, or is only partially immersed, the descent toward liquid nitrogen temperature can be slowed or even reversed.

As shown in FIGS. 1 and 2, the preferred embodiment of the invention uses two assemblies in the chamber, a top assembly (1) and a bottom assembly (8). This was constructed as described below. The dimensions presented are examples, but any variations are equally suitable. The top assembly (1) is a brass cylinder 2 inches high, and 3 inches in diameter, with a copper plate soldered across the top (2) and a copper ¼ inch O.D. tube (3) soldered into a hole drilled in the center of the plate. A plastic hose (4) with a ¼ inch I.D. is placed over the top of the copper tube (3), and a valve (5) (the one we use operates by pinching the hose (4), however, any type of air-tight valve will work) is placed around the plastic hose to control dry gas flow. (The other end of the hose (4) is connected to a source (25) of dry gaseous room-temperature nitrogen or gaseous, room temperature helium.) All seals and solder joints are generally air-tight. Bent spring-loaded hair clips (6) hold any wires (not shown) coming from the sample chamber to the tube (3) so that they are out of the way and will not get caught on anything as the chamber is moved around. FIG. 1 is an exploded view of the invention. In FIG. 2, the invention is assembled.

The bottom assembly consists of a brass cylinder (7) with an I.D. slightly larger than the O.D. of the top cylinder. It is closed on one end, and has a lip at the bottom (8) with an I.D. slightly less than the O.D. of the top cylinder. A brass frame assembly (9), 1.3 inches high, is soldered to the closed end of the cylinder. This shelf is where the test fixture and sample (20) is placed and attached. When both assemblies are brought together, they are held in place by more specially-bent spring-loaded hair clips (10).

To operate, the sample (20) is firmly affixed to the top of the shelf assembly (9). All wires leading from the test fixture are placed in the slot in the bottom assembly. The top assembly is then placed into the bottom assembly, and is clipped in place with the hair-clips (10). The wires are clamped onto the copper tube with more bent hair-clips (6). The whole assembly is then lowered into a container which contains liquid nitrogen. This container must be large enough to accommodate the whole assembly and hold enough liquid nitrogen to at least partially cover the chamber. As the chamber sections (1) and (8) descend into the container (200) of liquid nitrogen (210) the valve (5) is opened and dry (i.e. moisture-free) helium or dry nitrogen (hereafter referred to as "dry gas") is allowed to flow into the chamber. This action clears out any moisture-laden air and replaces it with dry gas which will not contaminate the sample. After a few seconds, the dry gas flow is turned off, and the chamber is immersed in the liquid nitrogen. A little liquid nitrogen will probably enter the bottom of the chamber as there is not an air tight seal between the two sections (1) and (8) of the chamber. A little care must be taken to ensure the chamber remains relatively upright in the liquid nitrogen so that dry gas remains trapped inside the chamber and keeps the liquid nitrogen (210) away from the sample.

The sample (20) will now rapidly cool to near liquid nitrogen temperatures.

After the cooling and testing is complete, the dry gas flow is started again by opening the valve either just before or just after the chamber sections (1) and (8) are raised above the liquid nitrogen level. Raising the chamber sections (1) and (8) before opening the valve ensures minimal waste of liquid nitrogen (210), rather than having room-temperature air bubbling through it. However, opening the valve (5) while the chamber is under liquid nitrogen (210) may ensure less moisture is able to enter the chamber. The chamber is than taken completely out of the container of liquid nitrogen and is allowed to warm up, keeping the dry gas flowing through it until it is near room temperature. Placing the chamber on a wire rack and blowing hot air from a regular hair-dryer (35) or another external source of heat onto the bottom surface helps to warm the chamber quickly without overheating it.

The advantages are that the whole system is very inexpensive, costing only a few dollars in materials, and a small amount of fabrication time. The container that holds the liquid nitrogen in which the chamber is immersed can be simple, inexpensive, and small. (The only requirement is that it be large and deep enough to hold enough coolant and allow the chamber to be immersed in it.) There is no special equipment necessary to operate the chamber. The materials used for construction-brass tubing and metal, copper tubing, solder, hair-clips, plastic tubing, simple valves—are all readily available. Cooling and heating times are kept to Just a few minutes, in conjunction with reliably keeping the sample in a dry atmosphere and away from liquid nitrogen—a new feature. Packaging up the sample for test is simple and easy, and can be accomplished in seconds—a new feature.

In addition, there are commercially-available sample heaters which could be attached near the sample, and temperature controllers that will stabilize the temperature of the sample at desired temperatures above the liquid nitrogen temperature. This mode is particularly useful for testing temperature-dependent material properties.

This chamber can be immersed in liquid helium for lower temperatures. However, the copper tubing would need to be replaced with stainless steel to ensure thermal isolation from the room-temperature air surrounding the top of the tube. Naturally, an insulated container that could accommodate the chamber assembly and liquid helium would also be required.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A cryogenic temperature adjustment system which can adjust a temperature of an object of interest to near cryogenic temperatures in a moisture-free environment, said cryogenic temperature adjustment system comprising:

a non-airtight chamber which holds the object of interest in an enclosed internal atmosphere of moisture-free gas;

a container of a cryogenic liquid which contains said non-airtight container and which can lower the temperature of the object of interest when the chamber is placed at least partially within the container;

a means of supplying the chamber with said moisture-free gas;

a means for providing ingress of a cryogenic liquid into the container when it vaporizes off due to heat exchange with the object of interest; and a means for placing the non-airtight chamber within the container.

2. A cryogenic temperature adjustment system, as defined in claim 1, which further comprises a means for heating the chamber and object of interest back to near room temperature when required.

3. A cryogenic temperature adjustment system, as defined in claim 2, wherein said supplying means comprises:

a supply of a moisture-free gas such as helium, dry nitrogen; and a means for adjusting a flow of said moisture-free gas between said supply and said chamber.

4. A cryogenic temperature adjustment system, as defined in claim 3, wherein said chamber comprises:

shell which can be attached to said adjusting means to receive said internal atmosphere of moisture-free gas;

a frame which is enclosed within said shell upon which said object of interest is placed; and a means which connects the shell to the adjusting means.

5. A cryogenic temperature adjustment system, as defined in claim 1, further including a supplying means which comprises:

a supply of moisture-free gas which as dry nitrogen; and a means for adjusting a flow of said moisture-free gas between said supply and said chamber.

6. A cryogenic temperature adjustment system, as defined in claim 5, wherein said chamber comprises:

a shell which can be attached to said adjusting means to receive said internal atmosphere of moisture-free gas;

a frame which is enclosed within said shell upon which said object of interest is placed; and a means which connects the shell to the adjusting means.

7. A cryogenic temperature adjustment system which can adjust a temperature of an object of interest to near cryogenic temperatures in a moisture-free environment, said cryogenic temperature adjustment system comprising;

a non-airtight chamber which holds the object of interest in an enclosed internal atmosphere of moisture-free gas;

a container of a cryogenic liquid which can lower the temperature of the object of interest when the chamber is placed within the container;

a means of supplying the chamber with said moisture-free gas;

a means for providing ingress of a cryogenic liquid into the container when it vaporizes off due to heat exchange with said object of interest;

a means for heating the chamber and object of interest back to near room temperature when required;

a supply of a moisture-free gas such as helium; and a means for adjusting a flow of said moisture-free gas between said supply and said chamber.

* * * * *